United States Patent [19]

McAndless

[11] 4,047,505
[45] Sept. 13, 1977

[54] INSECT REPELLENT COLLAR

[75] Inventor: John Madden McAndless, Ottawa, Canada

[73] Assignee: Canada, Her Majesty the Queen in right of, as represented by the secretary of National Defence, Ottawa, Canada

[21] Appl. No.: 710,606

[22] Filed: Aug. 2, 1976

[51] Int. Cl.² .............................................. A01K 27/00
[52] U.S. Cl. .................................... 119/106; 119/156; 424/125
[58] Field of Search ...................... 119/106, 156, 160; 239/54, 60; 424/125

[56] References Cited

U.S. PATENT DOCUMENTS

| | | | |
|---|---|---|---|
| 2,219,847 | 10/1940 | Purdum | 424/125 |
| 3,574,150 | 4/1971 | Jefferson et al. | 260/2.5 |
| 3,811,413 | 5/1974 | Scherpenborg | 119/156 |
| 3,814,061 | 6/1974 | Aries et al. | 119/106 |

Primary Examiner—Hugh B. Chamblee
Attorney, Agent, or Firm—D. Paul Weaver

[57] ABSTRACT

A device is disclosed for protection of a wearer's exposed skin against biting insects, and consists of a collar having a backing strip resistant to passage of liquid therethrough, an absorbent layer of open-cell solid resin foam impregnated with finely divided absorbent, and an outer porous covering. Liquid insect repellent is applied to the collar and absorbed, but then desorbs and evaporates at a slow rate to provide efficient protection when the collar is worn. Longer term protection using less chemical repellent than conventional methods is provided.

7 Claims, 2 Drawing Figures

INSECT REPELLENT COLLAR

This invention relates to a method and device for protecting a wearer's exposed skin against biting insects and more particularly relates to a collar of special construction to which a liquid insect repellent chemical is applied.

Insect repelling chemicals are of course very commonly used for protection against biting insects such as mosquitoes, blackflies and tabanids. Conventionally, repellents as for example N,N-diethyl-metatoluamide, or 2-ethyl-1,3-hexanedoil, are applied in liquid, spray, or cream form directly to exposed skin and require frequent and extensive application to be really effective. As the chemical evaporates, is rubbed off or is absorbed by the skin efficiency of protection is of course decreased. Some people may also develop skin rashes or irritation on continued use of insect repellents. Generally, these chemicals are hazardous to health if swallowed and direct use around the eyes, eyelids, lips or skin lesions is inadvisable. Furthermore, some of these chemicals also degrade and soften, for example synthetic fabrics, plastics and other materials on contact.

Another method of protection against biting insects which does not involve chemical repellents is of course the use of netting or other physical barriers. When worn around the head, such materials impede movement, restrict vision and are uncomfortable when worn for any length of time.

It has now been found that protection of exposed skin of the face and neck against biting insects is afforded by a simple device which overcomes the inherent disadvantages of the methods of protection previously used. The device is comfortable to wear and does not require direct application of insect repellent chemical to the skin. It consists of a collar having a central absorbent layer capable of retaining a considerable quantity of chemical repellent which is slowly released. While the collar is being worn the chemical evaporates and is carried around the neck and head of the wearer by body-heated air currents. Longer term protection of exposed skin is therefore provided using far less chemical repellent, and direct application to the skin is unnecessary. Once the repellent has been applied to the collar, re-application is unnecessary for several weeks. When the collar is not in use, it is easily stored in any convenient container.

The aforementioned device and method of protection against insects depend on the properties of the absorbent layer utilized in the collar construction. It has been found that open-cell resin foamed materials impregnated with suitable particulate absorbent, of the type described in Canadian Pat. No. 878,560, provide the properties of absorption of relatively large amounts of the insect-repelling chemical, and release of the chemical at a slow rate by desorption and evaporation over a period of time but in amounts which provide efficient protection against insects. These absorbent materials will be described in detail later herein.

Thus, the invention provides a collar for use in protecting exposed skin of a wearer's face and neck against biting insects which comprises:

a. a backing strip resistant to the passage of liquid therethrough and having fastening means at the ends thereof, b. an absorbent layer adjacent the backing strip and being formed of an open-cell solid resin foam impregnated with a finely divided particulate absorbent material capable of absorbing liquid insect repellent chemical which then slowly desorbs and evaporates, and c. a porous outer covering adjacent the absorbent layer and being secured to the backing strip.

The construction of a collar according to the invention is illustrated in the drawings, wherein.

Figures 1, 2:
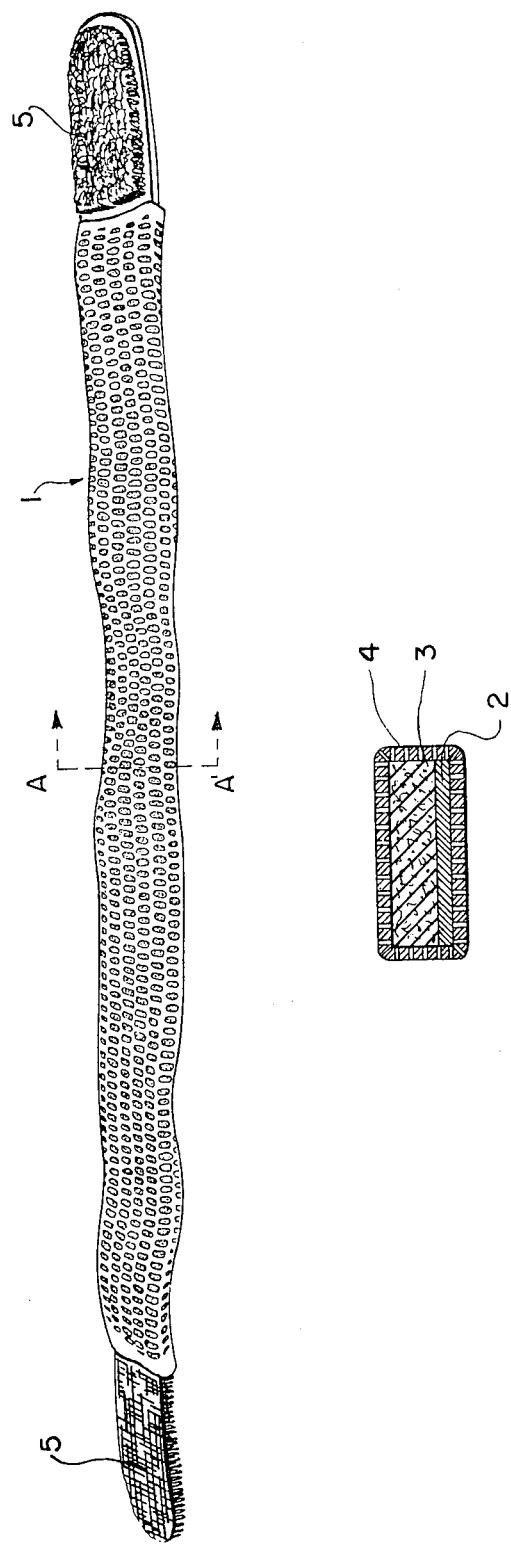
FIG. 1 is a plan view of the collar laid flat.
FIG. 2 is a vertical cross-section along the line A-A' of FIG. 1 in the direction of the arrows.

In the drawings, collar 1 consists of a backing strip 2 of for example fabric of low permeability or fabric treated to repel liquid, an absorbent middle layer 3 of a strip of open-cell foamed resin material impregnated with particulate absorbent material as for example polyurethane foam impregnated with activated charcoal, and an outer covering 4 of porous material such as wide mesh nylon fabric netting. The middle layer 3 may be laminated to the backing strip of may be retained in place by the outer covering 4 which is secured to the backing strip suitably by sewing. The outer covering 4 may extend behind the backing strip and partially or completely across it and is shown in FIG. 2 as extending behind and completely across the backing strip. Backing strip 2 is shown in FIG. 1 provided at its ends with fastening means consisting of "Velcro*" strips 5.

* Trade Mark

In use, insect repellent in liquid form is applied to the porous outer covering of the collar on the surface which is worn away from the skin, and as the liquid penetrates into the foamed resin layer, it is abosrbed and retained by the finely divided particulate absorbent material dispersed therein. The particulate material provides a large surface area and thus considerable amounts of chemical can be absorbed relatively quickly. However, the absorbent material allows slow desorption of the insect repelling chemical. Thus, when the collar is worn the chemical desorbs, and evaporates, and the vapors are carried upward about the neck and face of the wearer by body heated air currents, providing the protection against insects. The backing strip of the collar may be of low permeability or be pretreated with a liquid repellent agent to substantially prevent any unnecessary direct contact of the chemical with the skin underneath the collar by providing a further barrier. The backing strip provides mechanical strength to the collar construction which should however be flexible, and the backing strip also forms a base for the attachment of the other components.

Rigid and flexible open-cell foamed resin material impregnated with particulate absorbent are the subject of Canadian Pat. No. 878,560 which relates to protection against noxious chemicals such as warfare agents, industrial poisons and insecticides. It is disclosed that these materials are intended as protective barriers to be utilized in for example protective clothing and are for the purpose of preventing contact of the chemical liquid or vapor with the skin. For that purpose, it is disclosed that foamed materials may also be impregnated with substances to deactivate any desorbed chemical.

However, the aforementioned foamed materials have now been found to be suitable for use with insect repellents according to the present invention as they absorb relatively large quantities of the liquid repellent but permit desorption and evaporation of the repellent chemical at a controlled rate which provides efficient protection against insects over a considerable period of time. The particulate absorbent material enables absorption of relatively large amounts of the liquid chemical to provide a reservoir and vapor source but the open-cell foam effectively controls the rate of liquid evaporation by virtue of its structure. This combination as used in the collar according to the present invention enable highly efficient use of liquid insect repellent.

The finely divided particulate absorbent material is impregnated into the foamed resin by known techniques using binders as described in the aforementioned Canadian patent. For instance, the foam may be immersed in a suspension of the absorbent material in appropriate medium to which the binder has also been added. Then the foam is squeezed, pressed, or subjected to vacuum techniques to remove excess liquid and dried to cure the binder.

The particulate absorbent material for the purposes of the present invention is preferably activated charcoal but other suitable absorbents are alumina, silica gel, and active clays of the attapulgite and bentonite classes, as for example fuller's earth. This material may be dispersed in any open-cell foamed resin material provided of course, that the foamed material itself is not affected by the chemical repellent or any solvent in which it may be dissolved for application. Although polyurethane foams of the polyester type are preferred, other suitable foamed materials are polyurethane of the polyether type, cellulose, polystyrene, vinyl polymers and ployesters. Suitable binders are as indicated in Canadian Pat. No. 878,560 provided of course that these also are not affected by the chemical repellent or solvent in which it is dissolved. Examples are synthetic and natural rubber; polymers and copolymers of vinyl esters, vinyl acetals, acrylic esters, methacrylic esters, styrene, butadiene, acrylonitrile, chloroprene, ethylene and propylene; cellulose and starch derivatives; salts of alginic acid; and cellulose esters and ethers.

For the purposes of the present invention, the foamed material is suitably impregnated with the absorbent material in amounts of about 5-12 mg/cm$^2$. Foam density and cell size can be varied but it is evident that for the purposes of the present invention the material should not be too porous. An example of suitable porosity is 1.7 oz/sq. yd. foam weight with 100–110 cells/inch. Strips of absorbent material of about ⅛-⅜ inches in thickness are suitable for use in the collar according to the present invention. The particulate material should of course be dispersed in finely divided form in the foamed resin to provide a large surface area for absorbing the insect repellent. Preferred particle size of activated charcoal is 7–10 $\mu$ on the average.

The foamed material may be of the flexible or rigid type although the former is more suitable for the present purpose, as the collar construction should be sufficiently flexible for comfortable wearing. Flexible foams particularly lack strength per se, but in the collar according to the present invention the necessary mechanical strength is provided by the backing strip and also the outer covering attached thereto. Furthermore, the outer covering also protects the absorbent layer. If desired, the impregnated foamed resin layer may be laminated to the backing strip for further reinforcement by known techniques such as flame lamination, adhesive lamination, stitch bonding or quilting.

The backing strip is suitably of any material which can provide a barrier to the passage of liquid and is heavy enough to provide the required strength for the collar construction. Thus this material may be of a heavy tightly woven fabric which has low permeability, as for example heavy nylon-cotton blend fabric strapping or it may be a lighter more permeable fabric treated with liquid repellent agent. The latter is preferred for the purposes of the present invention and a variety of fabrics, as for instance cotton and cotton blends, may be treated according to conventional techniques with a liquid repellent agent, and utilized as the backing strip.

The outer covering for the collar should be a porous as possible to allow penetration of liquid insect repellent applied thereto into the absorbent layer. Also the outer covering must be porous to allow ready passage of the desorbed vaporized repellent.

The fastenings for the collar may be of any suitable known type, although "Velcro" strips as illustrated in the drawings are preferred for simplicity. Provision can be made so that the collar is adjustable in size by the length or positioning of the fastening means. Also, of course, the collars can readily be constructed in different sizes.

Especially useful as the insect repellent to be applied to the collar is a 75% by weight solution of N,N-diethyl-meta-toluamide in isopropanol. Other repellents can of course be used instead and examples of suitable compositions containing other known insect repellents are 50-75%/wt. alcohol solutions of benzyl benzoate, 2-ethyl-1,3-hexanediol, dimethyl phthalate, dimethyl carbate, alkyl sulfonyl pyrrolidone derivatives, 2,2,2-trichloro-N-pentyl acetamide, alkyl malate, alkyl fumarate and alkyl mandelate esters, and mixtures thereof.

The invention is illustrated in the following example which is, however, not to be taken as limiting.

EXAMPLE

Cotton twill tape (Corticelli (Canada) Ltd., size 10), one inch wide, was saturated with a mixture containing 15 parts Scotchgard FC-210 (a trade mark for a nonionic fluorochemical resin emulsion with a nominal solids content of 30% suppled by Minnesota Mining and Manufacturing Co.), 2 parts isobutanol and 83 parts water. Excess liquid was removed by passing the tape through the rolls of a padding mangle. The treated tape as air dried and then cured at 150° C. for 5 minutes. When tested by the Hydrocarbon Resistance Test 118-1966 of the American Association of Textile Chemists and Colorists, the oil repellency rating of the treated material was found to be 5, indicating a high level of repellency. A drop of N,N-diethyl-meta-toluamide placed on the treated page did not wet the fabric after standing for a period of 24 hours.

An impregnating bath for the absorbent layer of the collar was made up as follows. 5 parts casein and 1 part ammonia, s.g. 920, were mixed with 200 parts water and stirred until the casein dissolved. 100 parts of activated charcoal, type BPL, (a trademark of Pittsburg Chemical Company) was stirred into the suspension until the charcoal was completely dispersed. The charcoal was wet ball milled before addition to the suspension to a mass median diameter of 2.5 microns with 98% by weight smaller than 7 microns. 50 parts of an acrylic elastomer latex Hycar 2671 (a trademark of B.F. Goodrich Company) and 94 parts of water were added and mixed to povide a suspension containing 25% by weight of charcoal. This suspension was subsequently employed for impregnating the foam material for use in the collar.

Unsupported polyester type polyurethane foam, 5/32 inches in thickness, 100-110 cells per inch, weight 1.7 oz/sq yd was saturated in the carboncontaining suspension. Excess liquid was removed by passing the foam through the squeeze rolls of a padding mangle. The impregnated foam was then heated at 150° C for 10 minutes to cure the binder. The impregnation process was once again repeated to yield polyurethane foam containing activated charcoal in the amount of 7.5 mg/cm².

Mating "Velcro" fasteners, 2½ inches in length, were sewn on the ends of a 20 inch length of the treated cotton tape. A strip, 1 by 15 inches of the charcoal impregnated polyurethane foam prepared as described herein was centered on the cotton tape. The collar asssembly was covered by a 2¼ inches by 15 inches piece of nylon fishnet (Marion Textiles (U.S.), Pattern 467), weight 5.4 oz/sq. yd., 5–7 meshes per inch, and the netting joined lengthwise on the underside of the cotton tape backing strip by sewing. The edges of the netting were secured by sewing to the backing strip and to the inside edges of the Velcro fasteners.

The collar was then activated by brushing 4–6 cc. of a 75%/wt. solution of N,N-diethyl-m-toluamide in isopropanol evenly over the upper surface of the collar netting. The repellent-treated collar was allowed to stand for four hours before wearing and when worn provided protection against biting insects. The collar was stored in a foil-lined paper bag when not in use.

The embodiments of the invention in which an exclusive property or privilege is claimed are defined as follows:

1. A collar for use in protecting exposed skin of a wearer's face and neck against biting insets which comprises:

a. a backing strip resistant to the passage of liquid therethrough having a fastening means at the ends thereof,
   b. an absorbent layer adjacent the backing strip and being formed of an open-cell solid resin foam impregnated with a finely divided particulate absorbent material capable of absorbing liquid-repellent chemical which then slowly desorbs and evaporates, the rate of evaporation being controlled by the structure of the resin foam
   c. a porous outer covering adjacent the absorbent layer and being secured to the backing strip, and
   d. N, N-diethyl-meta-toluamide insect repellent applied to the porous outer covering adjacent the absorbent layer.

2. A collar as claimed in claim 1, wherein the absorbent layer is open-cell foamed polyurethane impregnated with finely divided activated charcoal.

3. A collar as claimed in claim 2, wherein the polyurethane foam is impregnated with about 5–12 mg/cm² of activated charcoal.

4. A collar as claimed in claim 1, wherein the foamed absorbent layer is a flexible foam laminated to the backing strip and is of a thickness of about ⅛–⅜ inches.

5. The collar as claimed in claim 1, wherein the backing strip is a fabric pretreated with liquid repellent agent.

6. A collar as claimed in claim 1, wherein the outer covering is a wide-mesh nylon fabric.

7. A collar as claimed in claim 1, wherein the resin foam has a porosity expressed as 1.7 ounces per square yard foam weight and 100–110 cells per inch.

* * * * *